United States Patent [19]

Maeda et al.

[11] 4,046,001
[45] Sept. 6, 1977

[54] APPARATUS FOR MEASURING RESTORING FORCE NECESSARY FOR RAISING FOLDED PORTIONS OF HARD PAPER BOXES

[75] Inventors: Fumiaki Maeda; Seiji Naruse, both of Chiba; Ko Kamiya, Ichikawa, all of Japan

[73] Assignees: Lion Fat & Oil Co. Limited; Toyo Sieki Seisakusho Ltd., both of Tokyo, Japan

[21] Appl. No.: 590,915

[22] Filed: June 27, 1975

[30] Foreign Application Priority Data

July 2, 1974 Japan .............................. 49-78501[U]

[51] Int. Cl.² .......................... G01N 3/22; G01L 5/12; B31B 5/74
[52] U.S. Cl. .................................. 73/100; 73/141 R; 93/53 SD
[58] Field of Search .................... 73/88 R, 100, 141 R, 73/141 A, 141 AB; 93/53 SD, 53 AC; 270/61 R, 68, 69; 269/21

[56] References Cited

U.S. PATENT DOCUMENTS

| | | | |
|---|---|---|---|
| 2,646,679 | 7/1953 | Buker | 73/100 |
| 2,782,695 | 2/1957 | Meissner et al. | 93/53 AC |
| 2,949,770 | 8/1960 | Kernan et al. | 73/100 X |
| 3,449,947 | 6/1969 | Ormond | 73/141 R X |
| 3,504,530 | 4/1970 | McConnell | 73/141 R X |
| 3,840,961 | 10/1974 | Brown | 269/21 |
| 3,905,592 | 9/1975 | Spencer et al. | 270/61 R |

*Primary Examiner*—Richard C. Queisser
*Assistant Examiner*—John S. Appleman
*Attorney, Agent, or Firm*—Stevens, Davis, Miller & Mosher

[57] ABSTRACT

An apparatus for measuring a restoring force necessary for raising folded portions of a hard paper box is disclosed. The apparatus comprises a base plate to which is attracted one folded portion of the hard paper box by means of vacuum, a hollow rotary wing to which is attracted another folded portion of the hard paper box by means of vacuum, means for rotating the hollow rotary wing together with said another folded portion around a ruled folded line edge formed between said one folded portion and said another folded portion, said one folded portion attracted to said base plate being kept stationary, and means for measuring difference between a force necessary for rotating said hollow rotary wing under no load condition and a force necessary for rotating said hollow rotary wing under a load condition.

9 Claims, 11 Drawing Figures

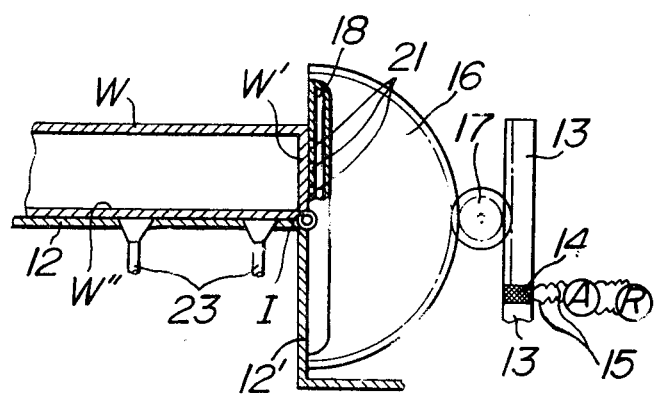
FIG_6
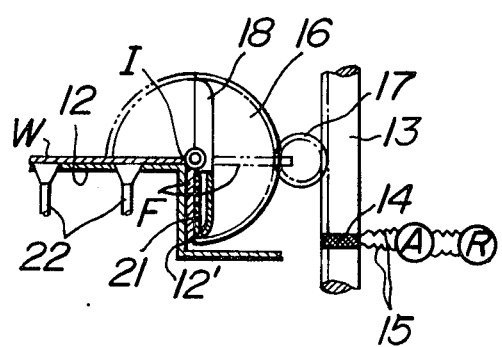
FIG_7

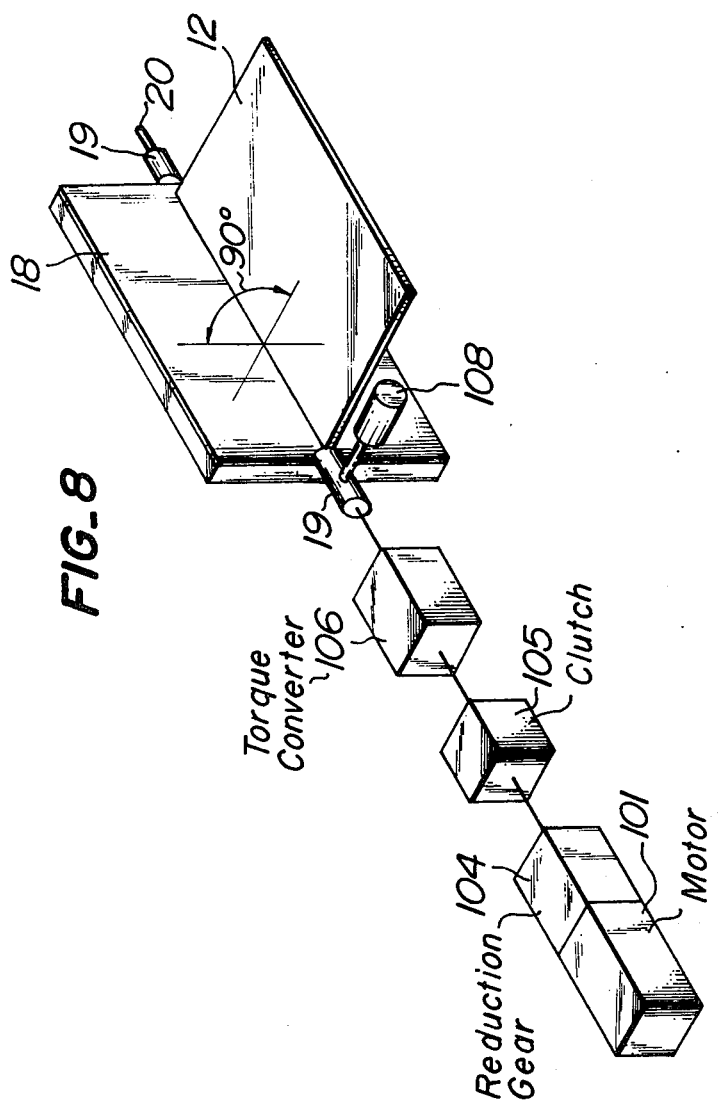

FIG_10
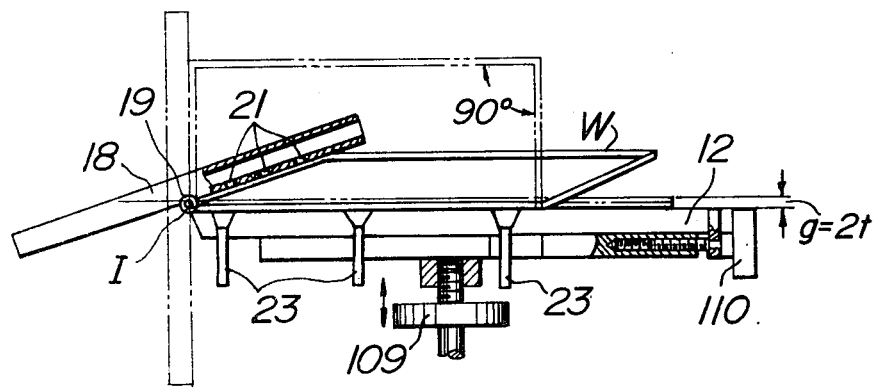
FIG_11
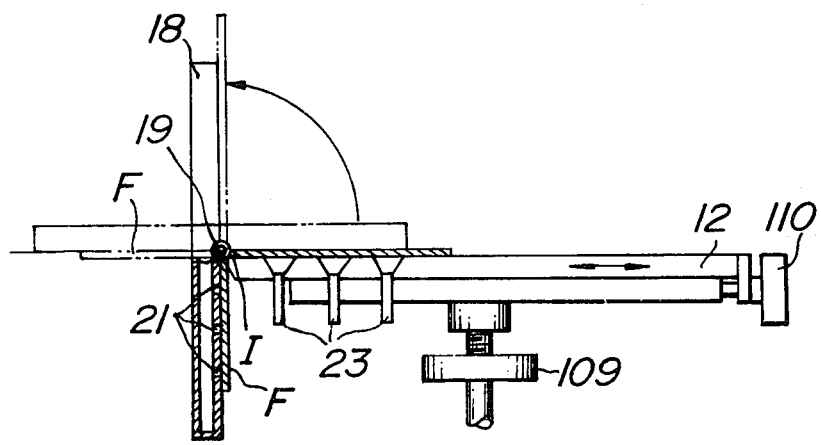

APPARATUS FOR MEASURING RESTORING FORCE NECESSARY FOR RAISING FOLDED PORTIONS OF HARD PAPER BOXES

This invention relates to an apparatus for measuring a restoring force necessary for raising folded portions of hard paper boxes such as a carton box, a corrugated cardboard box and the like that are used to pack powder and granular detergents and a folded flap thereof as well as a folded portion of a file that is used to arrange paper, cards or letters in a particular order for preservation and reference.

A rectangular carton box, for example, that is used to pack powder or granular detergents therein is folded flat for shipment to the user. This flat folded carton box is charged into an automatic packing machine by which the flat folded carton box is restored to its original rectangular carton box with its base flaps folded as they are to close the base and with its top flaps opened to form an opening. Then, a predetermined amount of powder or granular detergent is charged through the open top opening of the rectangular carton box therein and subsequently the open top flaps are folded to close the open top opening and provide a rectangular carton box with the powder or granular detergents packed therein.

When restoring the folded flat carton box into its original rectangular form, it is necessary to measure a restoring force necessary for raising folded portions of the carton box.

In order to measure such restoring force, a compression testing machine shown in FIG. 1 has heretofore been proposed. In such conventional compression testing machines, upper and lower ruled folded line edges of a folded carton box W being tested are held between an upper stationary supporting member 1 and a slidably movable base plate 2. Then, the base plate 2 is moved upwardly from the full line position to the dot and dash lines position to restore the test piece W into its rectangular shape as shown by dot and dash lines. The restoring force of the four ruled folded line edges I can be measured with the aid of a recorder R connected through conductors 3 and an amplifier A to a piezoelectric element or strain gauge 4 sandwiched between an upper stationary portion and a lower movable portion of the stationary supporting member 1.

As seen from the above, such a conventional compression testing machine makes use of a compressive force subjected to the upper and lower ruled folded line edges I, I in a direction along a straight line common to both the upper and lower ruled folded line edges, I, I, and as a result, has the disadvantage that there is a risk of the test piece W being deformed upon being subjected to the compressive force and hence the real restoring force necessary for raising folded portions of the carton box W could not be measured.

An object of the invention is to provide an apparatus which is simple in construction and reliable in operation and which can measure a real restoring force necessary for raising folded portions of hard paper boxes without causing any deformation thereof during measurement.

A feature of the invention is the provision of an apparatus for measuring a restoring force necessary for raising folded portions of a hard paper box, comprising
a framework;
a base plate for disposing thereon a hard paper box having ruled folded line edges formed between small and large portions and slidably supported by said framework and including a plurality of suction nozzles each extending through said base plate and opened at the top surface thereof;
means for adjusting the position of said base plate;
a hollow rotary wing including an interior space, a plurality of suction holes formed in the base of said wing and a hollow center shaft rotatably supporting said wing at that center of said wing which makes contact with a hard paper box to be tested and having a suction tube extended therethrough and communicated with said interior space;
a vacuum supply source communicated with said suction nozzles of said base plate on the one hand and with said suction holes of said hollow rotary wing on the other hand;
means for rotating said hollow rotary wing; and
a detector means for detecting a difference between a force necessary for rotating said hollow rotary wing under no load condition and a force necessary for rotating said hollow rotary wing under a load condition.

The invention will now be described in greater detail with reference to the accompanying drawings, wherein:

FIG. 6 shows similarly to FIG. 4 a front elevation of the apparatus shown in FIG. 2, in which the hollow rotary wing is rotated by 90° to raise the folded carton box;

FIG. 7 shows a front elevation of the apparatus shown in FIG. 2, showing a flap of the carton box sandwiched between the hollow rotary wing and the base plate;

FIG. 8 is a perspective view of another embodiment of the apparatus according to the invention;

FIG. 10 is a front elevation of the apparatus shown in FIG. 8, showing the hollow rotary wing slightly rotated to raise a folded carton box sandwiched between the hollow rotary wing and the base plate; and FIG. 11 is a front elevation of the apparatus shown in FIG. 8, showing a flap of the folded carton box sandwiched between the hollow rotatable wing and the base plate.

Figure 2:
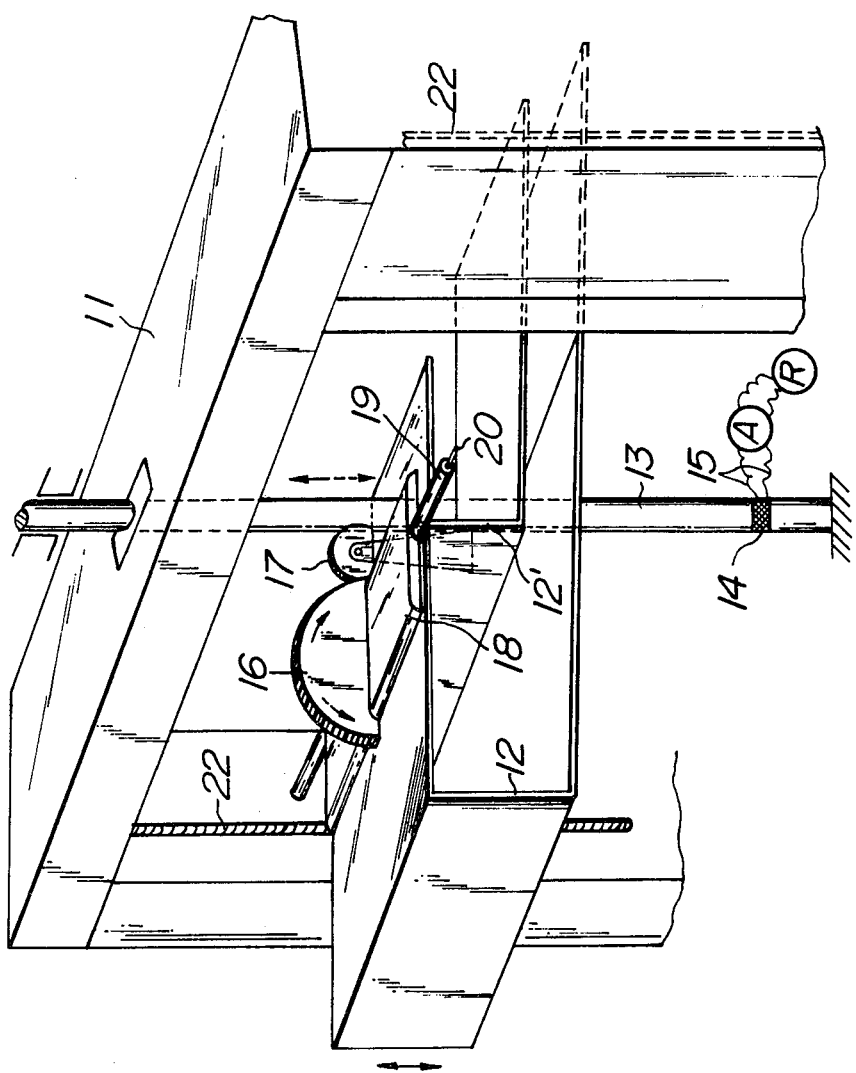
FIG. 2 is a perspective view of one embodiment of an apparatus for measuring a restoring force necessary for raising folded portions of hard paper boxes and files according to the invention.

Referring to FIG. 2, reference numeral 11 designates a framework for slidably supporting a base plate 12 of an apparatus according to the invention and 13 a rack divided into two portions, the upper portion being slidably supported by the framework 11 and the lower portion being secured through a piezoelectric element, strain gauge and the like 14 to the framework 11, said piezoelectric element 14 being connected through conductors 15, an amplifier A to a recorder R which can detect a thrust force subjected to the piezoelectric element 14.

Reference numeral 16 designates a semi-circular gear engaged through a pinion 17 with the rack 13 and provided at its base portion with a hollow rotary wing 18 extending across diametrically opposite ends of the semicircular gear 16 and made integral therewith. The hollow rotary wing 18 is rotatably supported by and communicated with a hollow rotary shaft 19. The interior space of the hollow rotary wing 18 is subjected to a negative pressure or vacuum which is supplied thereto through a suction tube 20 extending through the shaft 19 and connected to a vacuum source (not shown) for the purpose of attracting the hard paper box to be tested.

Figure 3:
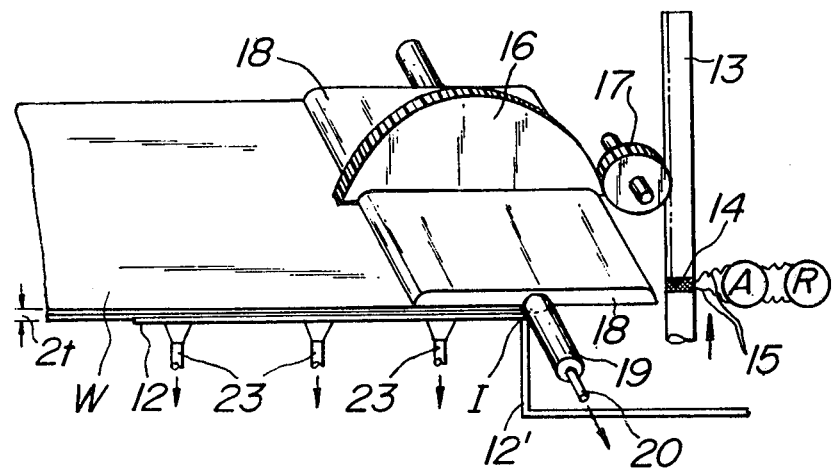
FIG. 3 is a perspective view of essential parts of the apparatus shown in FIG. 2 with a folded carton box sandwiched between a hollow rotatable wing and a base plate.
Figure 4:
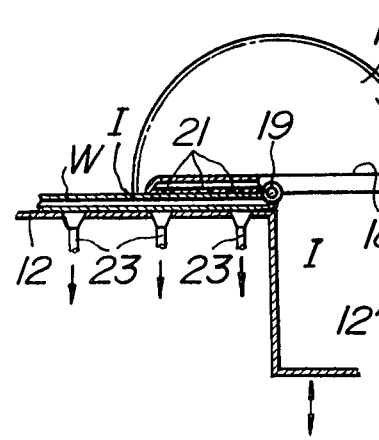
FIG. 4 is a front elevation of the apparatus shown in FIG. 2.
Figure 5:
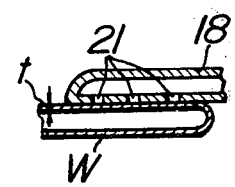
FIG. 5 is a section on line V—V of FIG. 3.

A folded carbon box W is sandwiched between the hollow rotary wing 18 and the base plate 12 as shown in FIGS. 3 and 4. The hollow rotary wing 18 is provided at that base surface which is opposed to the folded carton box W with a plurality of suction holes 21 which serve to attract the folded carton box W to the hollow rotary wing 18 by the negative pressure existing in an interior space of the hollow rotary wing 18. The position and size of the suction holes 21 may suitably be selected in dependence with the material and thickness t of the sheet of the folded carton box W.

That part 12' of the base plate 12 which is aligned with one of ruled folded line edges I of the folded carton box W is bent downwardly to form one edge of the base plate 12. The base plate 12 is provided at both of its sides with screws 22 (FIG. 2) which can raise and lower the base plate 12. The base plate 12 is provided at that surface which supports the folded carton box W with a plurality of suction nozzles 23 which are communicated with a vacuum source (not shown) and which can attract and secure the folded carton box W to the base plate 12.

The apparatus constructed as above described will operate as follows.

At first, as shown in FIG. 6, the hollow rotary wing 18 is maintained at its vertical position with its lower half abutted against the downwardly bent portion 12' of the base plate 12 and then means (not shown) are operated to lower the base plate 12 by a distance which is equal to twice times the thickness t of the folded carton box W. Then, the folded carton box W is disposed on the base plate 12 with one of ruled folded line edges I abutted against the base surface of the vertical hollow rotary wing 18. Then, the base plate 12 is moved upwardly to rotate through the pinion 17 and the semi-circular gear 16 the hollow rotary wing 18 by 90° to a position shown in FIG. 4. As a result, the folded carton box W is sandwiched between the hollow rotary wing 18 and the base plate 12 as shown in FIGS. 3 and 4.

Now, vacuum is applied through the suction holes 21 and suction nozzles 23 to attract the folded carton box W to both the hollow rotary wing 18 and the base plate 12. Then, the base plate 12 is moved downwardly to rotate through the pinion 17 and the semi-circular gear 16 the hollow rotary wing 18 by 90° from the position shown in FIGS. 3 and 4 to the position shown in FIG. 6. The rotation of the hollow rotary wing 18 by 90° causes that small portion W' of the folded carton box W attracted to the hollow rotary wing 5 to raise from its large portion attracted to the base plate 12 by 90°. The restoring force necessary for raising the small portions W' from the folded carton box W applies thrust force through the semi-circular gear 16, pinion 17 and the rack 13 to the piezoelectric element 14, and as a result, the piezoelectric element 14 delivers an electric signal through the conductors 15 and amplifier A to the recorder R which can detect the thrust force subjected to the piezoelectric element 14.

As a result, the restoring force necessary for restoring the folded carton box W from its folded position shown in FIG. 4 to the raised position shown in FIG. 6 can be detected by the recorder R by a difference between the electric signal delivered from the piezoelectric element 14 under no load condition and the electric signal delivered therefrom under a load condition.

When detecting the bending stress necessary for bending a flap F of the folded carton box W, the folded carton box W is disposed on the base plate 12 as shown by dot and dash lines in FIG. 7 with the flap F projected outwardly from the ruled folded line edge I. Then, the hollow rotary wing 18 is rotated by 90° from the position shown by dot and dash lines to the position shown by a full line in FIG. 7.

The bending stress required to bend the flap F around the ruled folded line edge I is transmitted through the semi-circular gear 16, pinion 17, and rack 13 to the piezoelectric element 14 to produce an electric signal therein. The electric signal delivered from the piezoelectric element 14 is transmitted through the conductors 15 and amplifier A to the recorder R which can detect a difference between a thrust force necessary for rotating the hollow rotary wing 18 under no load, that is, for rotating the hollow rotary wing 18 only and a thrust force necessary for rotating the hollow rotary wing 18 under load condition, that is, for rotating the rotary wing 18 together with the flap F.

In the above described embodiment of the invention, the apparatus according to the invention has been applied to measure the restoring force necessary for raising the folded portions of the folded carton box.

The apparatus according to the invention may also be applied to measure the restoring force necessary for raising the various kinds of folded hard boxes such as a folded corrugated cardboard box and the like as well as the restoring force necessary for raising a folded portion of files and the like.

As explained hereinbefore, the use of the measures described ensures rotation of a restoring force necessary for raising folded portions of a hard paper box in an arcuate direction around a ruled folded line edge I of the folded portions and further provides the important advantage that the real restoring force can precisely be measured, that the apparatus is extremely simple in construction, and that data usable for the operation of an automatic packing machine can be obtained.

In FIG. 8 is shown another embodiment of the apparatus according to the invention which makes use of a torque converter directly connected to the hollow rotary wing 18. In the present embodiment, a motor 101 is energized from an electric source 102 (FIG. 9) when a switch 103 is closed. The rotation of the motor 101 is transmitted through a reduction gear 104, a clutch 105 and a torque converter 106 to the hollow rotary wing 18. When the hollow rotary wing 18 disposed in that position which is opposed to the base plate 12 is rotated by 90° to a vertical position shown in FIG. 8, a limit switch 107 (FIG. 9) is operated to release the clutch 105 and at the same time to turn the switch 103 OFF to deenergize the motor 101.

The hollow rotary wing 18 is held at its balanced state by means of a balancing weight 108 (FIG. 8) disposed at right angles to the center axis of the hollow center shaft 19, and as a result, the hollow rotary wing 18 may be made stationary at any position within its rotatable range. In the present embodiment, the hollow center shaft 19 of the hollow rotary wing 18 is so journaled by a bearing (not shown) that there is no occurrence of frictional loss during the rotation of the hollow rotary wing 18.

As in the previous embodiment, the hollow rotary wing 18 is provided with the suction holes 21 and the base plate 12 is provided with the suction nozzles 23 for the purpose of attracting the test piece of the folded carton box W to both the hollow rotary wing 18 and the base plate 12, respectively.

When measuring the restoring force necessary for raising the folded carton box W, at first a test piece of the folded carton box W is disposed on the base plate 12 and then a knob 109 is operated to lower the base plate 12 to form a gap g having a thickness which is equal to two times the thickness t of the folded carton box W. Then, the hollow rotary wing 18 is rotated around its hollow center shaft 19 by 90° to a vertical position shown by dot and dash lines in FIG. 10. Subsequently, one of the ruled folded line edges I of the folded carton box W is placed in contact with the hollow rotary wing 18 by hand. Then, the hollow rotary wing 18 is rotated by 90° to the position disposed on the base plate 12 and the small and large surface portions of the folded carton box W are attracted to the hollow rotary wing 18 and the base plate 12 by vacuum applied through the suction holes 21 and suction nozzles 23, respectively. All of the above operations are manually effected.

If the switch 103 is closed to energize the motor 101 from the electric source 102, the motor 101 is operated to rotate the rotary hollow wing 18 in a counterclockwise direction in FIG. 10 to raise the folded carton box W. The restoring force necessary for raising the folded carton box W is converted into an electric signal by means of the torque converter 106. The electric signal from the torque converter 106 is delivered through a torque selector 111 to a recorder 112. When the folded carton box W is completely raised, that is, arrives at a position shown by dot and dash lines in FIG. 10, the limit switch 107 is operated to turn the switch 103 OFF, thereby stopping the motor 101. At the same time, the limit switch 107 serves to release the clutch 105, thereby automatically releasing the hollow rotary wing from the motor 101.

Figure 9:
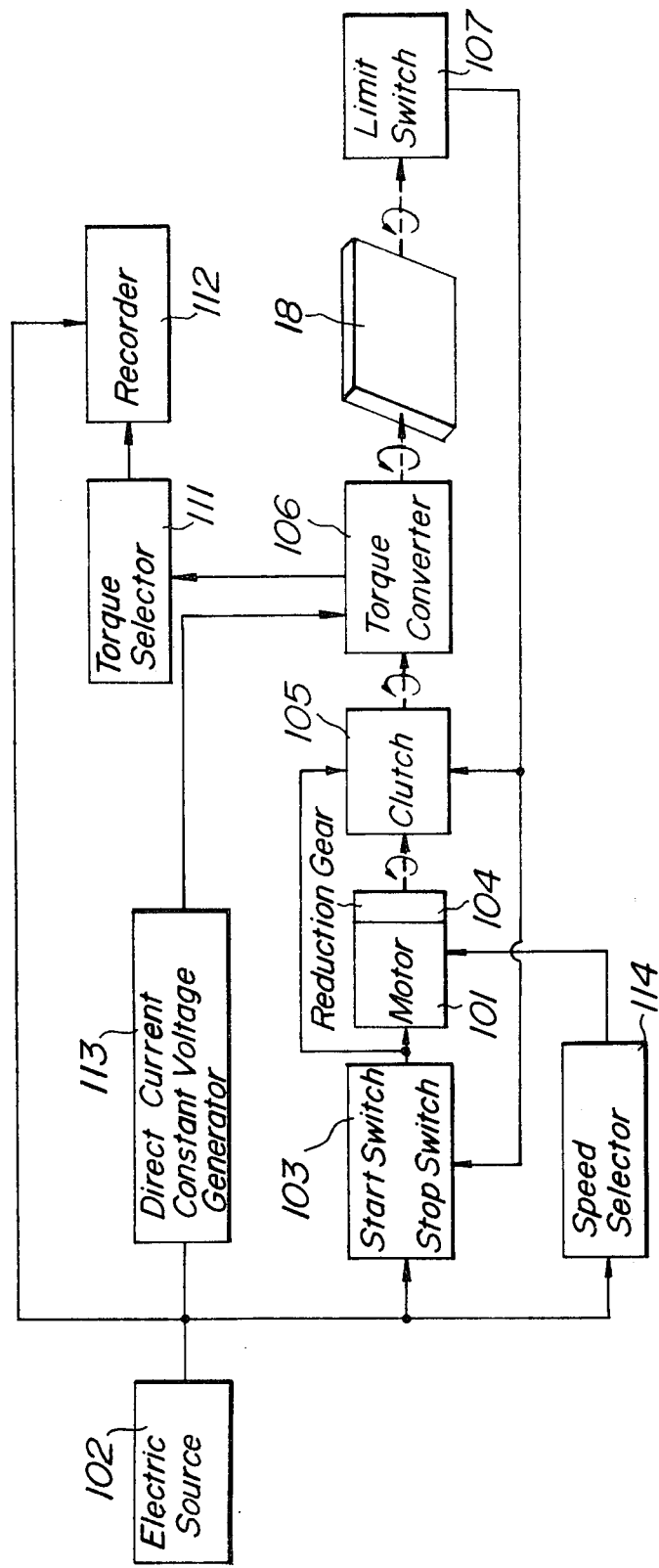
FIG. 9 is a block diagram of a control circuit usable for the apparatus shown in FIG. 8.

In FIG. 9, reference numeral 113 designates a direct current constant voltage generator, and 114 a speed selector.

Figure 1:
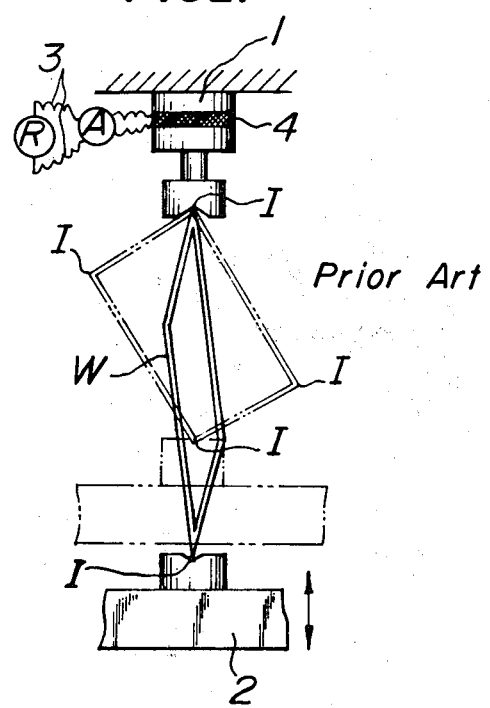
FIG. 1 is a front elevation of a prior art compression testing machine designed to measure a restoring force of folded portions of a folded carton box being tested.

As stated hereinbefore, the use of the measures described ensures detection of the restoring force necessary for raising the folded carton box W with the aid of a torque for rotating the hollow rotary wing 18 together with the small surface portion of the folded carton box W around the ruled folded line edge I formed at one end of the base plate 12 and provides the important advantage that only the restoring force necessary for raising the folded carton box W can be detected if compared with the conventional compression testing machine which makes use of a compression force against the opposed ruled folded line edges as shown in FIG. 1.

In the case of measuring the bending force necessary for vertically bending a horizontal flap F of the folded carton box W, the knob 109 is operated to lower the base plate 12 to form a gap g which is equal to the thickness t of a test piece of the flap F. Then, the hollow rotary wing 18 is rotated by 90° to a position shown by a full line in FIG. 11 and the base plate 12 is horizontally moved by means of the knob 110 to form a gap g between the center axis of the shaft 19 of the hollow rotary wing 18 and the front edge of the base plate 12, which is equal to the thickness t of the test piece of the flap F. Subsequently, the flap F is inserted between the hollow rotary wing 18 in the dot and dash lines position and the base plate 12 with the flap F projecting outwardly from one of the ruled folded line edges I is aligned with the front edge of the base plate 12. Then, vacuum is applied to the base plate 12 only to attract the folded carton box W to the base plate 12. If the starting switch 103 is closed, the bending force necessary for downwardly rotating the folded flap F from its horizontal position shown by dot and dash lines in FIG. 11 to the vertical position shown by a full line can be detected in the same manner as that described with reference to FIG. 10.

What is claimed is:

1. An apparatus for measuring a restoring force necessary for raising folded portions of a hard paper box, comprising
    a framework;
    a base plate for disposing thereon a hard paper box having ruled folded line edges formed between small and large portions and slidably supported by said framework and including a plurality of suction nozzles each extending through said base plate and opened at the top surface thereof;
    means for adjusting the position of said base plate;
    a hollow rotary wing including a base surface for sandwiching a folded box between said base surface and the base plate, an interior space, a plurality of suction holes formed in the base of said wing and a hollow center shaft rotatably supporting said wing at that center of said wing which makes contact with a hard paper box to be tested and having a suction tube extended therethrough and communicated with said interior space;
    a vacuum supply source communicated with said suction nozzles of said base plate on the one hand and with said suction holes of said hollow rotary wing on the other hand;
    means for rotating said hollow rotary wing; comprising a torque converter coupled to said hollow rotary wing on the one hand and to a driving motor for rotating said wing on the other hand and for producing an electric signal corresponding to a torque applied to said hollow rotary wing; and
    a detector means for detecting a force necessary for rotating said hollow rotary wing, including means for receiving said electric signal from said torque converter, and therefrom detecting a difference between a force for rotating said hollow rotary wing under no load condition and a force for rotating said hollow rotary wing under a loaded condition.

2. An apparatus according to claim 1, wherein said detector means comprises a recorder coupled to said torque converter for recording a difference between torques applied to said wing under no load and loaded conditions.

3. An apparatus according to claim 2, including a limit switch for detecting vertical displacement of said wing, and for interrupting the application of torque to said wing upon detecting a vertical displacement thereof.

4. An apparatus for measuring a restoring force necessary for raising folded portions of a hard paper box, comprising a framework;

a base plate for disposing thereon a hard paper box having ruled folded line edges formed between small and large portions and slidably supported by said framework and including a plurality of suction nozzles each extending through said base plate and opened at the top surface thereof;

means for adjusting the position of said base plate;

a hollow rotary wing including a base surface for sandwiching a folded box between said base surface and the base plate, an interior space, a plurality of suction holes formed in the base of said wing and a hollow center shaft rotatably supporting said wing at that center of said wing which makes contact with a hard paper box to be tested and having a suction tube extended therethrough and communicated with said interior space;

a vacuum supply source communicated with said suction nozzles of said base plate on the one hand and with said suction holes of said hollow rotary wing on the other hand;

means for rotating said hollow rotary wing, comprising a semi-circular gear made integral with said hollow rotary wing and vertically projecting therefrom and a rack divided into two portions, the upper portion being slidably supported by said framwork and the lower portion being secured to said framework; and a detector means for detecting a force necessary for rotating said hollow rotary wing, including means for detecting a difference between a force for rotating said hollow rotary wing under no load condition and a force for rotating said hollow rotary wing under a loaded condition, said detector means comprising a piezoelectric element, a strain gauge or the like sandwiched between said two portions of said rack and connected through an amplifier to a recorder.

5. An apparatus for measuring a restoring force necessary for raising folded portions of a hard paper box, comprising a framework;

a base plate for disposing thereon a hard paper box having ruled folded line edges formed between small and large portions and slidably supported by said framework and including a plurality of suction nozzles each extending through said base plate and opened at the top surface thereof;

means for adjusting the position of said base plate;

a hollow rotary wing including a base surface for sandwiching a folded box between said base surface and the base plate, an interior space, a plurality of suction holes formed in the base of said wing and a hollow center shaft rotatably supporting said wing at that center of said wing which makes contact with a hard paper box to be tested and having a suction tube extended therethrough and communicated with said interior space;

a vacuum supply source communicated with said suction nozzles of said base plate on the one hand and with said suction holes of said hollow rotary wing on the other hand;

means for rotating said hollow rotary wing, comprising a semi-circular gear made integral with said hollow rotary wing and vertically projecting therefrom and a rack divided into two portions, the upper portion being slidably supported by said framework and the lower portion being secured to said framework, and a detector means for detecting a force necessary for rotating said hollow rotary wing, said detector means comprising a pressure sensitive element located between said two portions of said rack, and a recorder coupled to said pressure sensitive element for recording said difference between forces.

6. An apparatus according to claim 5, wherein said base plate includes a part which is rectangularly stepped relative to a part of the base plate including the suction nozzles to form an edge at which a fold line of a box may be aligned.

7. An apparatus according to claim 6, wherein said base surface of said hollow rotary wing extends over the edge defined by the stepped part of said base plate, so that a flap of a box which projects outwardly over said edge may be bent at the time the hollow rotary wing rotates by 90°.

8. An apparatus according to claim 5, wherein said pressure sensitive element is a piezoelectric element.

9. An apparatus according to claim 5, wherein said pressure sensitive element is a strain guage.

* * * * *